United States Patent [19]

Takahashi et al.

[11] Patent Number: 4,991,565

[45] Date of Patent: Feb. 12, 1991

[54] SHEATH DEVICE FOR ENDOSCOPE AND FLUID CONDUIT CONNECTING STRUCTURE THEREFOR

[75] Inventors: Nagashige Takahashi; Teruo Ouchi, both of Tokyo, Japan

[73] Assignee: Asahi Kogaku Kogyo Kabushiki Kaisha, Tokyo, Japan

[21] Appl. No.: 537,984

[22] Filed: Jun. 13, 1990

[30] Foreign Application Priority Data

Jun. 26, 1989 [JP] Japan ................. 1-163114
Jun. 26, 1989 [JP] Japan ................. 1-163115
Jun. 26, 1989 [JP] Japan ................. 1-74613[U]

[51] Int. Cl.⁵ ............................. A61B 1/00
[52] U.S. Cl. ............................. 128/4
[58] Field of Search ................... 128/4, 6

[56] References Cited

U.S. PATENT DOCUMENTS

| | | | |
|---|---|---|---|
| 4,522,196 | 6/1985 | Cunningham et al. | 128/4 |
| 4,646,722 | 3/1987 | Silverstein et al. | 128/4 |
| 4,721,097 | 1/1988 | D'Amelio | 128/4 |
| 4,741,326 | 5/1988 | Sidall et al. | 128/4 |
| 4,771,766 | 9/1988 | Aoshiro et al. | 128/4 |
| 4,791,912 | 12/1988 | Tashiro | 128/4 |
| 4,807,593 | 2/1989 | Ito | 128/4 |
| 4,809,678 | 3/1989 | Klein | 128/4 |
| 4,815,450 | 3/1989 | Patel | 128/4 X |
| 4,878,485 | 11/1989 | Adair | 128/4 X |
| 4,944,287 | 7/1990 | Takahashi et al. | 128/4 |

*Primary Examiner*—William H. Grieb
*Attorney, Agent, or Firm*—Sandler, Greenblum & Bernstein

[57] ABSTRACT

An endoscope is provided with a sheath which is removably fitted over an insert tube to isolate it from the external environment. A plurality of channels are provided for passing fluids, each channel having an opening at one end near the distal end portion of the sheath and extending at the other end past the proximal end of the sheath. A channel connecting device is provided at the extending end portions of the channels. The channel connecting device is capable of simultaneously and detachably connecting at least two of the channels to respective channels in the endoscope through respective connecting conduits, which are provided in a control part of the endoscope. Respective end portions of the channels are disposed in substantially parallel relations to each other, and the connecting conduits are disposed in a direction which is perpendicular to the axes of the end portions of the channels. In addition, a packing is provided in an opening at the proximal end of the sheath which is movable in the radial direction of the sheath to enable the insert tube to be inserted into and removed from the sheath while the outer peripheral surface of the insert tube remains hermetically sealed.

25 Claims, 9 Drawing Sheets

SHEATH DEVICE FOR ENDOSCOPE AND FLUID CONDUIT CONNECTING STRUCTURE THEREFOR

BACKGROUND OF THE INVENTION

1. Field of the Invention

The present invention relates to a sheath device for an endoscope, which is fitted over an insert tube of the endoscope that is inserted into a hollow organ of the patient's body, the sheath device being designed so that a portion thereof which comes into contact with mucus and mucous membrane in a hollow organ of the patient's body can be disposed of after use for one endoscopic procedure. The present invention also relates to a fluid conduit connecting structure for use in the sheath device described above.

2. Description of the Prior Art

To prevent the transmission of bacteria or viruses from one patient to another through an endoscope, it is the most effective way to arrange an endoscope such that a portion thereof which comes into contact with mucus and mucous membranes in a hollow organ of the patient's body can be disposed of after use during one endoscopic procedure.

Among various portions that comprise an endoscope, those which come into contact with mucus and mucous membranes in a hollow organ of the patient's body include the outer surface of the insert tube and channels such as forceps suction, air and water channels. Accordingly, a typical conventional sheath device for an endoscope is designed so that a sheath which covers the insert tube and channels are disposable as one set.

However, control valves for control of the supply of air and water are generally provided in the control part of an endoscope. It is therefore necessary to disconnect channels, for example, air and water channels, from the control valves in the endoscope each time the endoscope has been used.

In this type of conventional sheath device for an endoscope, the channels that are provided in the sheath device are individually connected to the respective control valves in the endoscope. Accordingly, each channel must be disconnected from the corresponding control valve when the sheath device is to be removed from the endoscope (see U.S. Pat. No. 4,646,722).

Thus, a complicated and troublesome operation is required to connect and disconnect each channel, and it is exceedingly difficult to handle the sheath device. In consequence, a great deal of time is needed to remove the sheath device after use, and there is a danger that the endoscope may be contaminated during the removal of the sheath device.

In addition, since the channels must be adapted to be detachable with respect to the control valves, it is difficult to employ a valve mechanism which is commonly used in endoscopes, and a special valve mechanism must be prepared.

The connection of each pair of channels is generally effected through a metal pipe, for example, which is disposed along the axis of the channels which are connected together in a straight-line form. Accordingly, it is necessary to ensure a long space for the connection of the channels. As a result, the length of the control part of the endoscope increases, and hence the operability deteriorates.

One type of conventional sheath device for an endoscope is arranged such that the sheath is inflated with air when the insert tube of the endoscope is inserted into and removed from the sheath in order to enable the insert tube to be smoothly inserted and removed. In this type of sheath device, the insert tube of the endoscope is inserted into and removed from the sheath through a packing which is provided in an opening at the proximal end of the sheath. In the prior art, the packing is fixedly provided in the opening at the proximal end of the sheath.

In consequence, when the insert tube of the endoscope bends, the packing which is pushed by the insert tube is deformed to produce a gap through which air leaks out. When the insert tube of the endoscope, which is in a state where no turning force is applied thereto, is turned about its axis, a gap is produced between the packing and the insert tube, resulting in air leaking out through the gap.

If air leaks out from the sheath, the sheath deflates; in such a case, not only the insert tube of the endoscope is caught in the sheath and cannot be smoothly inserted or removed, but also the sheath may be broken.

SUMMARY OF THE INVENTION

An object of the present invention is to provide a sheath device for an endoscope, which is designed so that channels which are provided in the sheath device can be readily connected to and disconnected from respective conduits in the endoscope and can also be readily connected to a conventional valve mechanism for endoscopes.

Another object of the present invention is to provide a compact fluid conduit connecting structure which is capable of connecting together channels that are provided in an endoscope and channels that are provided in a sheath device without increasing the overall size of the control part of the endoscope.

Another object of the present invention is to provide a sheath device for an endoscope, which is designed so that the insert tube of the endoscope can be smoothly inserted into and removed from the sheath without causing leakage of air from the sheath.

Other objects and advantages of the present invention will become apparent from the following detailed description of illustrated embodiments of the invention.

According to the present invention, there is provided a a sheath device for an endoscope, which removably covers an insert tube of the endoscope to isolate the insert tube from the external environment, comprising: a sheath which is removably fitted over the insert tube to isolate it from the external environment; a plurality of channels for passing fluids, each channel opening at one end thereof to the outside at the distal end portion of the sheath; and a channel connecting device which is provided at the proximal end portions of the channels and which is capable of simultaneously connecting at least two of the channels to respective conduits in the endoscope.

In addition, there is provided a structure for connecting fluid conduits in an endoscope, comprising: a fluid supply channel which is disposed inside a control part of the endoscope; a fluid sending channel which is provided in a sheath device that removably covers an insert tube of the endoscope, to send out fluid that is supplied from the fluid supply channel; and a channel connecting device for connecting together the fluid supply channel and the fluid sending channel through a connecting conduit in the control part of the endoscope, with the respective end portions of the channels being disposed substantially parallel to each other, and the connecting conduit being disposed in a direction which is perpendicular to the axes of the end portions of the channels.

In addition, there is provided a sheath device for an endoscope, which removably covers an insert tube of the endoscope to isolate the insert tube from the external environment, comprising: an airproof sheath which removably covers the insert tube; and a packing which is provided in an opening at the proximal end of the sheath in such a manner as to be movable in the radial direction of the sheath to enable the insert tube to be inserted into and removed from the sheath with the outer peripheral surface of the insert tube being hermetically sealed, without any gap between the packing and the outer peripheral surface of the insert tube.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below in detail with reference to the accompanying drawings.

Figure 1:
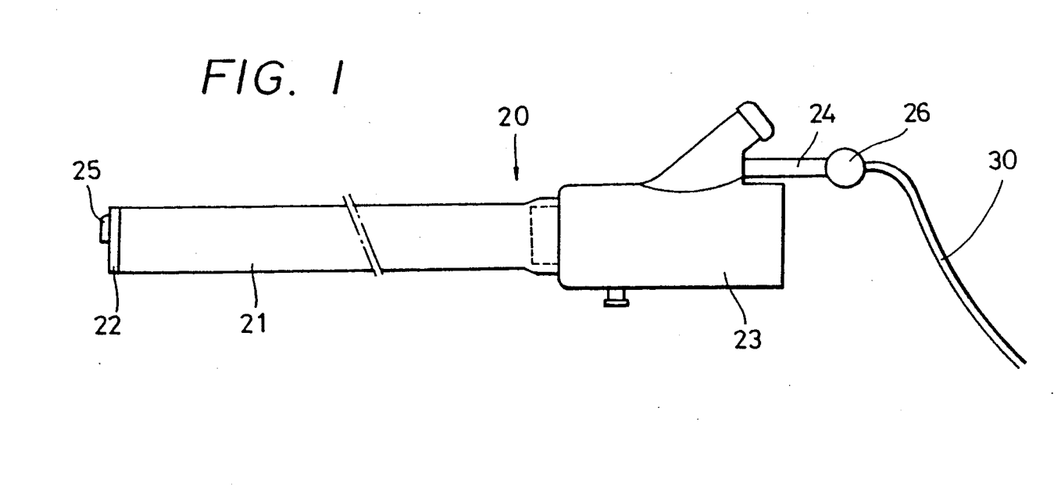
FIG. 1 is a side view of one embodiment of the sheath device for an endoscope according to the present invention.
Figure 2:
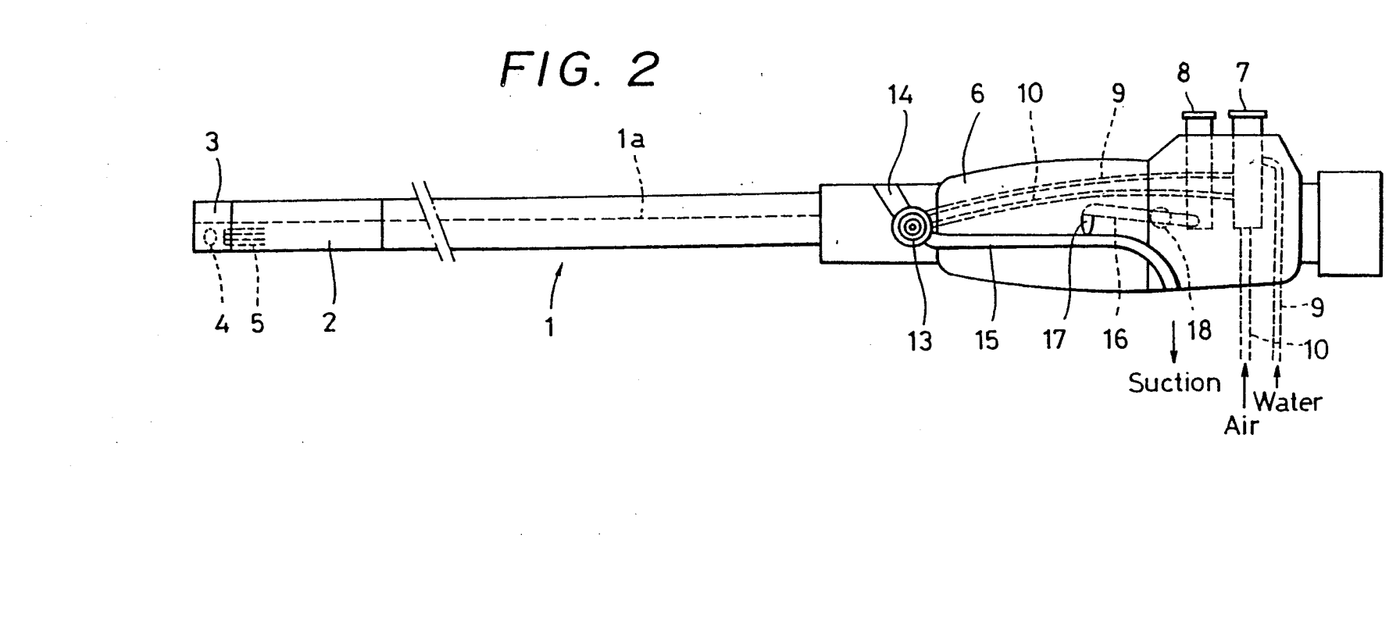
FIG. 2 is a side view of an endoscope which is inserted into the sheath device according to the present invention.

FIG. 1 shows one embodiment of the sheath device for an endoscope, and FIG. 2 shows an endoscope which is inserted into the sheath device that is shown in FIG. 1.

Referring to FIG. 2, the endoscope has an insert tube 1 which is formed from an elongated flexible tube. A bendable portion 2 is formed at the distal end of the insert tube 1, the portion 2 being bendable by remote control. A distal end tip 3 is provided at the distal end of the bendable portion 2. An objective lens 4 is disposed inside the distal end tip 3, and the incident end face of an image guide fiber bundle 5 is disposed at the imagery position of the objective lens 4.

Figure 5:
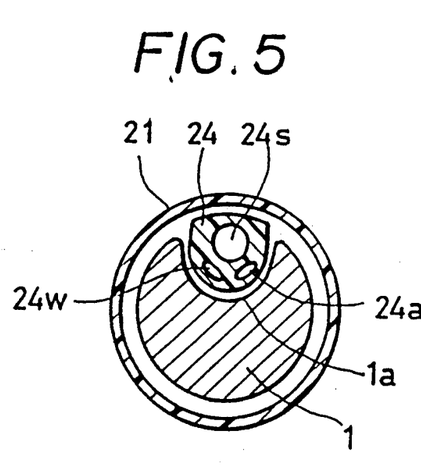
FIG. 5 is an enlarged sectional view taken along the line V—V in FIG. 3.

A U-shaped groove 1a such as that shown in FIG. 5 is continuously formed in the respective outer peripheral surfaces of the insert tube 1, the bendable portion 2 and the distal end tip 3 in such a manner as to extend straight along the axis of the insert tube 1.

Referring back to FIG. 2, a control part 6 is coupled to the proximal end portion of the insert tube 1. The control part 6 is provided with an air and water control valve 7 for controlling the supply of air and water, a suction control valve 8 for controlling suction, and a bending control device (not shown) for controlling bending of the bendable portion 2. It should be noted that the respective positions of the air and water control valve 7 and the suction control valve 8, which are shown in FIG. 2, may be exchanged.

Reference numeral 9 denotes a water supply channel through which water is supplied, and 10 an air supply channel through which air is supplied. The channels 9 and 10 comprise a fluid supply channel.

These channels 9 and 10 are connected at their outer ends to air and water tanks (not shown) and supplied with air and water, respectively. The channels 9 and 10 extend through the control part 6 and are connected at their distal ends to a connector socket 13 that is provided in the control part 6, the socket 13 opening on the surface of the control part 6.

Reference numeral 20 in FIG. 1 denotes a sheath of the sheath device, which is removably fitted over the insert tube 1 of the endoscope to isolate it from the external environment. The sheath 20 comprises a tubular portion 21, a distal end portion 22 and a mouth portion 23.

Figure 3:
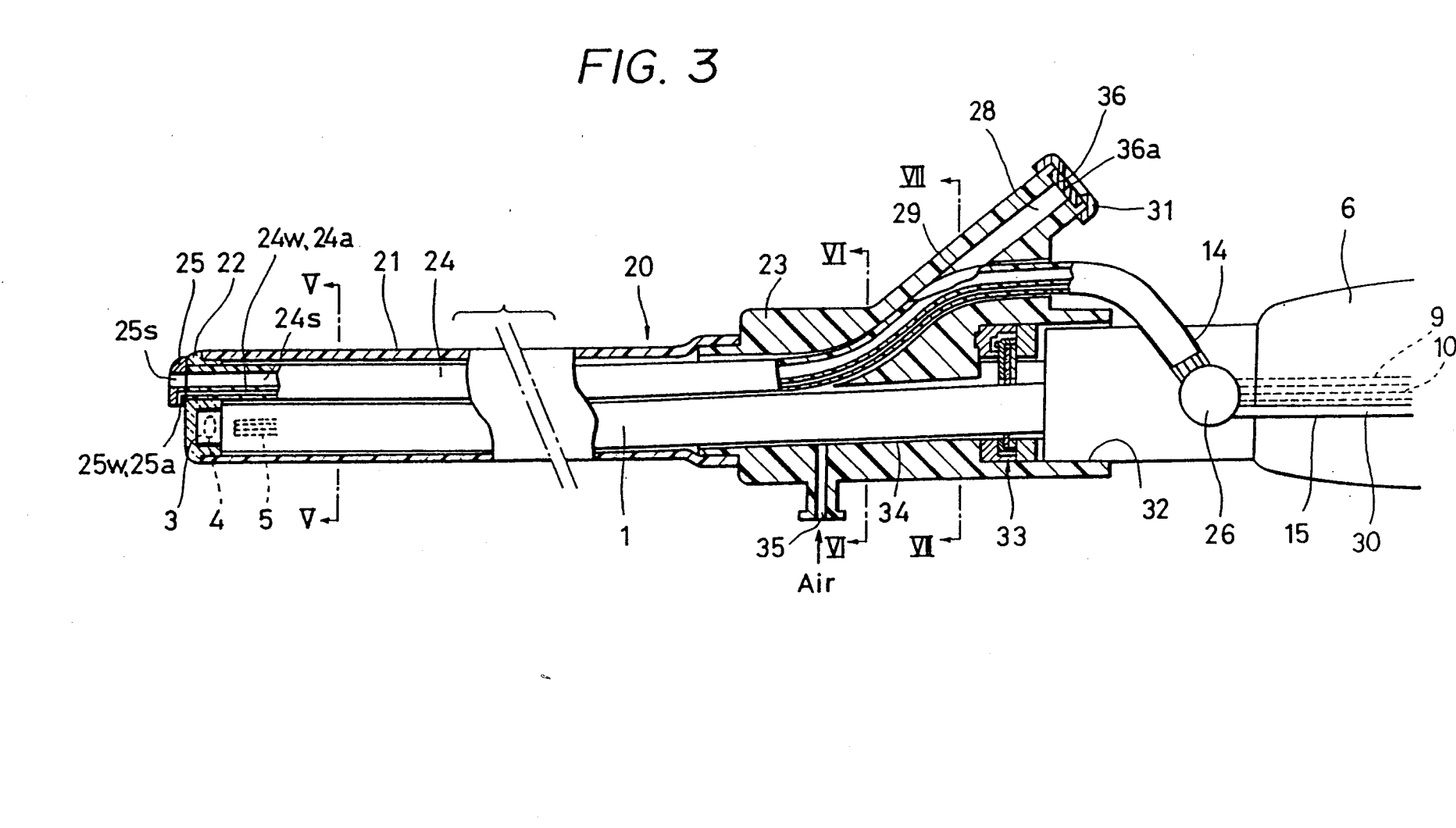
FIG. 3 is a sectional side view of the endoscope in a state where it is inserted in the sheath device according to the present invention

FIG. 3 shows the insert tube 1 of the endoscope in a state where it is inserted into the sheath 20.

The tubular portion 21 of the sheath 20 is formed in the shape of a thin-walled cylinder using an elastic material, for example, silicone rubber, and the distal end portion 22, which is formed from a transparent material, for example, a transparent styrol resin material, is connected to the distal end of the tubular portion 21 in such a manner that no air leaks out from the sheath 20. The rear end of the tubular portion 21 is firmly bonded to the distal end of the mouth portion 23 in such a manner that no air leaks out from the sheath 20. It should be noted that the inner diameter of the tubular portion 21 is smaller than the outer diameter of the insert tube 1 so that the tubular portion 21 tightly fits over the insert tube 1.

A channel tube 24, which is made of, for example, tetrafluoroethylene resin, extends through the sheath 20 over the entire length thereof. The channel tube 24 has a suction channel 24s which also serves as a forceps channel, an air sending channel, 24a and a water sending channel 24w (see FIG. 5). The channel tube 24 is disposed along the groove 1a in the outer surface of the insert tube 1 of the endoscope. The air sending channel 24a and the water sending channel 24w comprise a fluid sending channel. In FIG. 5, illustration of the details of the cross-sectional structure of the insert tube 1 is omitted.

The rear end portion of the channel tube 24 extends from the rear end of the mouth portion 23, and a channel connector 26 is connected to the end of the channel tube 24. Thus, the channel tube 24 can be detachably connected to the connector socket 13, shown in FIG. 2, through the connector 26. Reference numeral 30 denotes a suction channel tube that extends from the channel connector 26.

Figure 4:
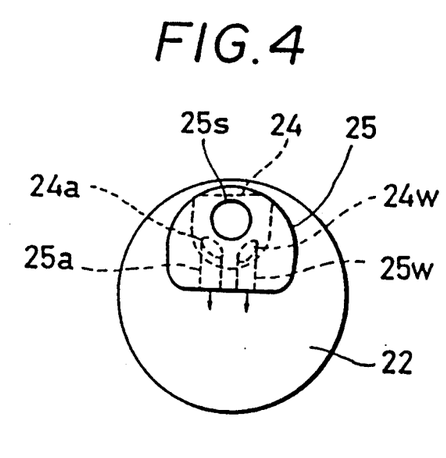
FIG. 4 is an enlarged front view of the distal end portion of the sheath device according to the present invention.

The distal end portion 22 is formed such that the distal end tip 3 is loosely fitted therein. A nozzle piece 25 projects from the end face of the distal end portion 22. As shown in FIG. 4, the nozzle piece 25 is provided with an air nozzle 25a and a water nozzle 25w. The nozzles 25a and 25w are formed so as to face a viewing window that is formed in the distal end tip 3 when the distal end tip 3 is inserted into the distal end portion 22.

The nozzle piece 25 is further provided with a suction opening 25s, also serving as a forceps opening, which opens forwardly. The suction channel 24s, the air sending channel 24a and the water sending channel 24w are communicated with the suction opening 25s, the air nozzle 25a and the water nozzle 25w, respectively.

Reference numeral 28 FIG. 3 denotes a forceps inserting bore which is provided in a projecting portion of the mouth portion 23. A disk-shaped rubber forceps stopper 36 is fitted into the mouth of the forceps inserting bore 28, the forceps stopper 36 having, for example, a - shaped slit 36a that is formed in the center thereof. A cap 31 is detachably attached to the mouth of the forceps inserting bore 28 to hold the forceps stopper 36.

Figure 7:
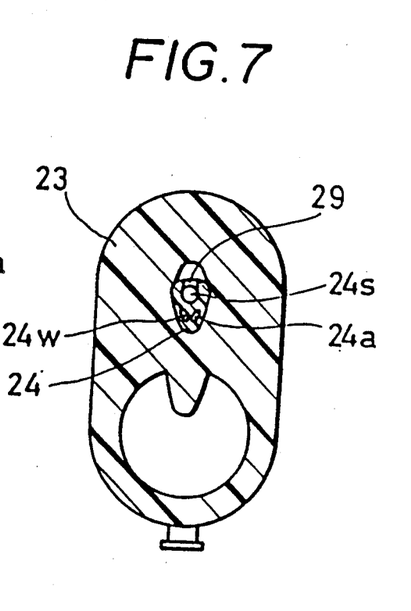
FIG. 7 is a sectional view taken along the line VII—VII in FIG. 3.

The side wall of the channel tube 24 is provided with a bore 29 that provides communication between the suction channel 24s and the forceps inserting bore 28, as shown in FIG. 7. Accordingly, a tool for an endoscopic procedure, for example, a biopsy forceps, can be inserted into the suction channel 24s from the forceps inserting bore 28 through the slit 36a in the forceps stopper 36 in such a manner that no air leaks out from the sheath 20.

Figure 6:
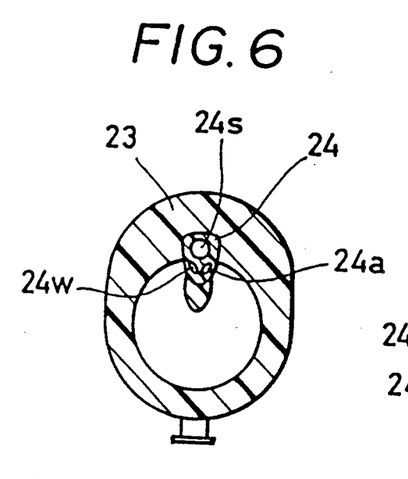
FIG. 6 is a sectional view taken along the line VI—VI in FIG. 3.

FIG. 6 is a sectional view taken along the line VI—VI in FIG. 3. In FIGS. 6 and 7, illustration of the insert tube 1 of the endoscope is omitted.

Referring back to FIG. 3, the proximal end of the extending portion of the channel tube 24 is detachably fitted into a channel tube guide groove 14 that is formed in the side wall of the control part 6. The channel connector 26, which is connected to the extending end portion of the channel tube 24, is detachably connected to the connector socket 13.

The suction channel tube 30 is detachably fitted into a suction channel guide groove 15 (also shown in FIG. 2) that is formed in the side wall of the control part 6. The suction channel tube 30 extends outside the control part 6 and is connected to, for example, a suction device (not shown). Reference numeral 17 in FIG. 2 denotes a suction control pin, which is activated to open and close the suction channel tube 30 in response to the action of the suction control valve 8 through a control arm 16 that pivots about a pin support shaft 18.

Figure 8:
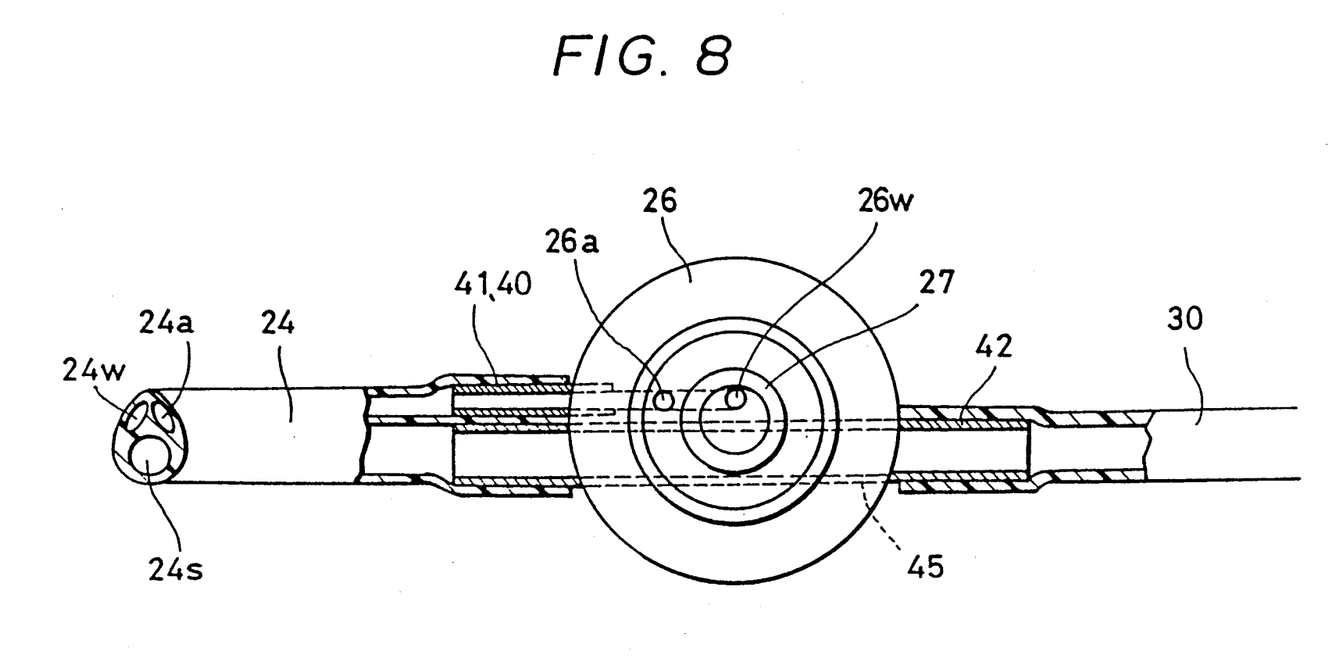
FIG. 8 is a partially-cutaway bottom view showing a channel connector.

The channel connector 26 and the connector socket 13 will next be explained with reference to FIGS. 8 and 9.

The channel connector 26 is formed from an elastic rubber or synthetic resin material. The channel connector 26 has air and water conduits 26a and 26w, which bend at right angles. The water sending channel 24w and the air sending channel 24a are connected to the outer ends of the conduits 26w and 26a through connecting pipes 40 and 41, respectively. The channel connector 26 has a connecting tubular portion 27 which projects therefrom at the inner end of the water conduit 26w. Reference numeral 26c denotes a click engagement projection which prevents the channel connector 26 from coming off the connector socket 13.

The channel connector 26 further has a through-bore 45 which extends straight therethrough. A connecting pipe 42 is inserted into the through-bore 45 to connect together the suction channel 24s in the channel tube 24 and the suction channel tube 30, which is connected to an external suction device.

Figure 9:
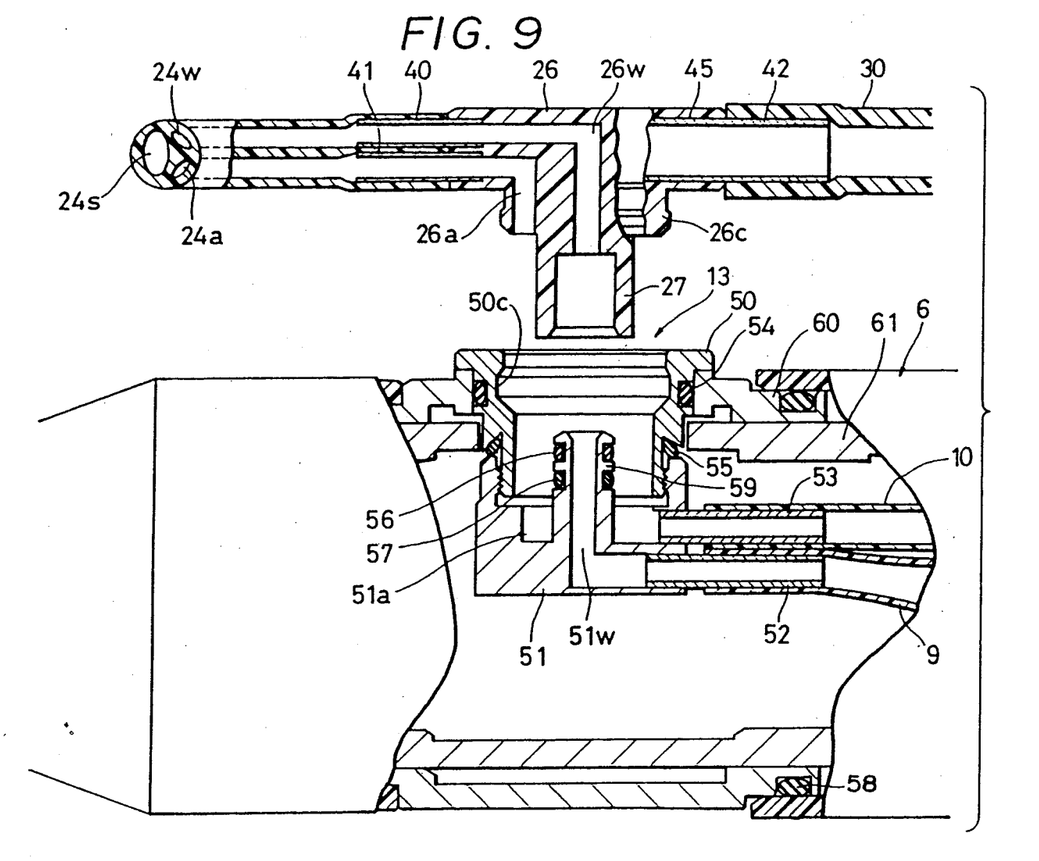
FIG. 9 is an enlarged sectional side view of the channel connector and a connector socket.

As shown in FIG. 9, the connector socket 13 comprises a socket member 50 and a bottom member 51, which are in thread engagement with each other, these members 50 and 51 being formed from a stainless steel, for example.

The socket member 50 is supported by a support tube 60 that is fixed between a frame 61 of the control part 6 and a cover for the control part 6. The socket member 50 opens outwardly and has a click engagement recess 50c which is formed in the inner wall of its mouth.

The bottom member 51 has two, inner and outer, conduits 51w and 51a, which are partitioned off from each other by a connecting tube 59. The tubular portion 27 of the channel connector 26 is connected to the connecting tube 59. The conduits 51w and 51a are bent at right angles and connected to the water and air supply channels 9 and 10 through connecting pipes 52 and 53, respectively.

Thus, the end portions of the water and air supply channels 9 and 10 in the endoscope and those of the water and air sending channels 24w and 24a in the sheath device are disposed in substantially parallel to each other, and the conduits 51w and 51a for connecting the corresponding end portions of these channels extend in a direction which is perpendicular to the axes of the end portions of the channels. Reference numerals 54, 55, 56, 57 and 58 denote O-rings for sealing.

Figure 10:
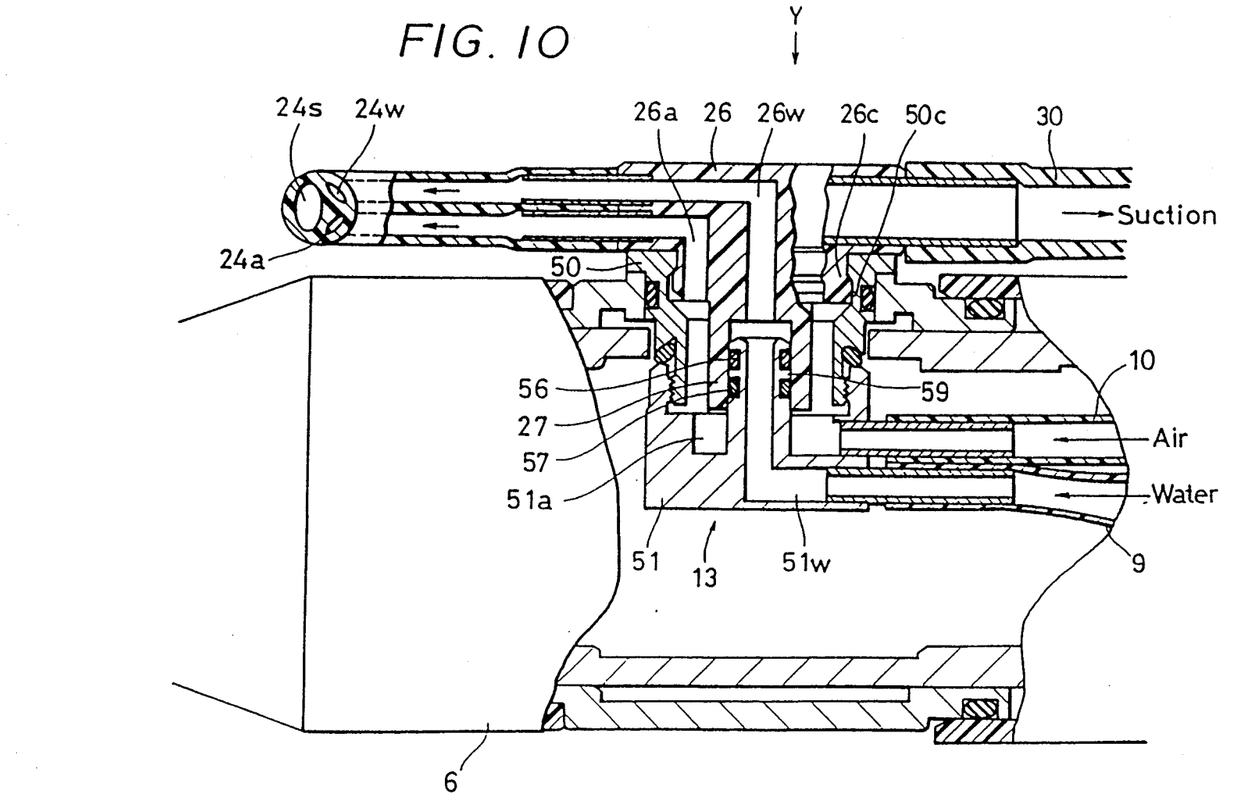
FIG. 10 is an enlarged sectional side view of the channel connector and the connector socket, which are connected together.

FIG. 10 shows the channel connector 26 in a state where it is connected to the connector socket 13. The connection of the channel connector 26 is effected by forcing the channel connector 26 into the connector socket 13 in the direction of the arrow Y, that is, in a direction which is perpendicular to the axes of the channels 24a, 24w, 9 and 10. Since the channel connector 26 is elastic, the projection 26c and the recess 50c in the socket member 50 are clicked into engagement with each other, thereby enabling the channel connector 26 to be detachably connected to the connector socket 13.

In this connected state, the water conduits 51w and 26w are connected together through the O-rings 56 and 57 in such a manner that no water will leak out. Thus, the water supply channel 9 and the water sending channel 24w are connected together. Similarly, the air conduits 51a and 26a are connected together in such a manner that no air will leak out, and the air supply channel 10 and the air sending channel 24a are thus connected together.

Referring back to FIG. 3, a structure for inserting the insert tube 1 of the endoscope into the mouth portion 23 will be explained. Reference numeral 32 denotes a control part inserting bore which opens at the proximal end of the mouth portion 23. When the insert tube 1 of the endoscope has been completely inserted into the sheath 20, the end portion of the control part 6 of the endoscope loosely fits in the control part inserting bore 32. A packing unit 33 is disposed in the inner part of the control part inserting bore 32 to prevent air from leaking out from the sheath 20 when the insert tube 1 is inserted into or removed from the sheath 20.

An insert tube inserting bore 34, which communicates with the control part inserting bore 32, extends straight in the tubular portion 21. Reference numeral 35 denotes an air supply opening for externally supplying air into the sheath 20 to inflate the tubular portion 21.

Figure 11:
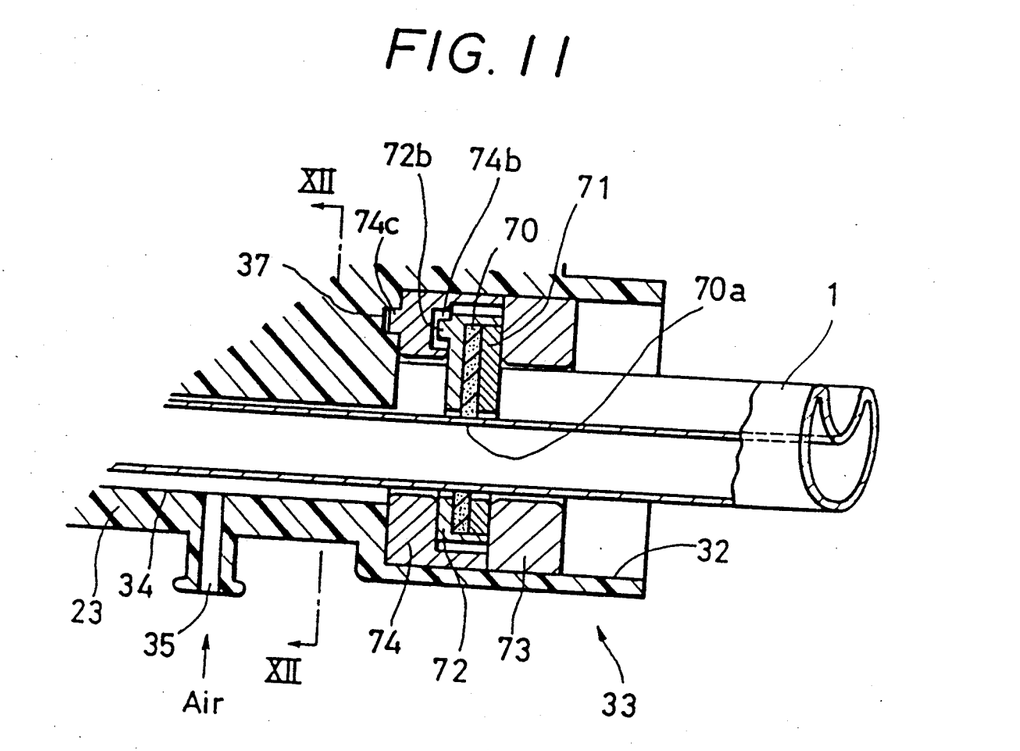
FIG. 11 is an enlarged sectional side view of a packing unit that is employed in the sheath device according to the present invention.
Figure 13:
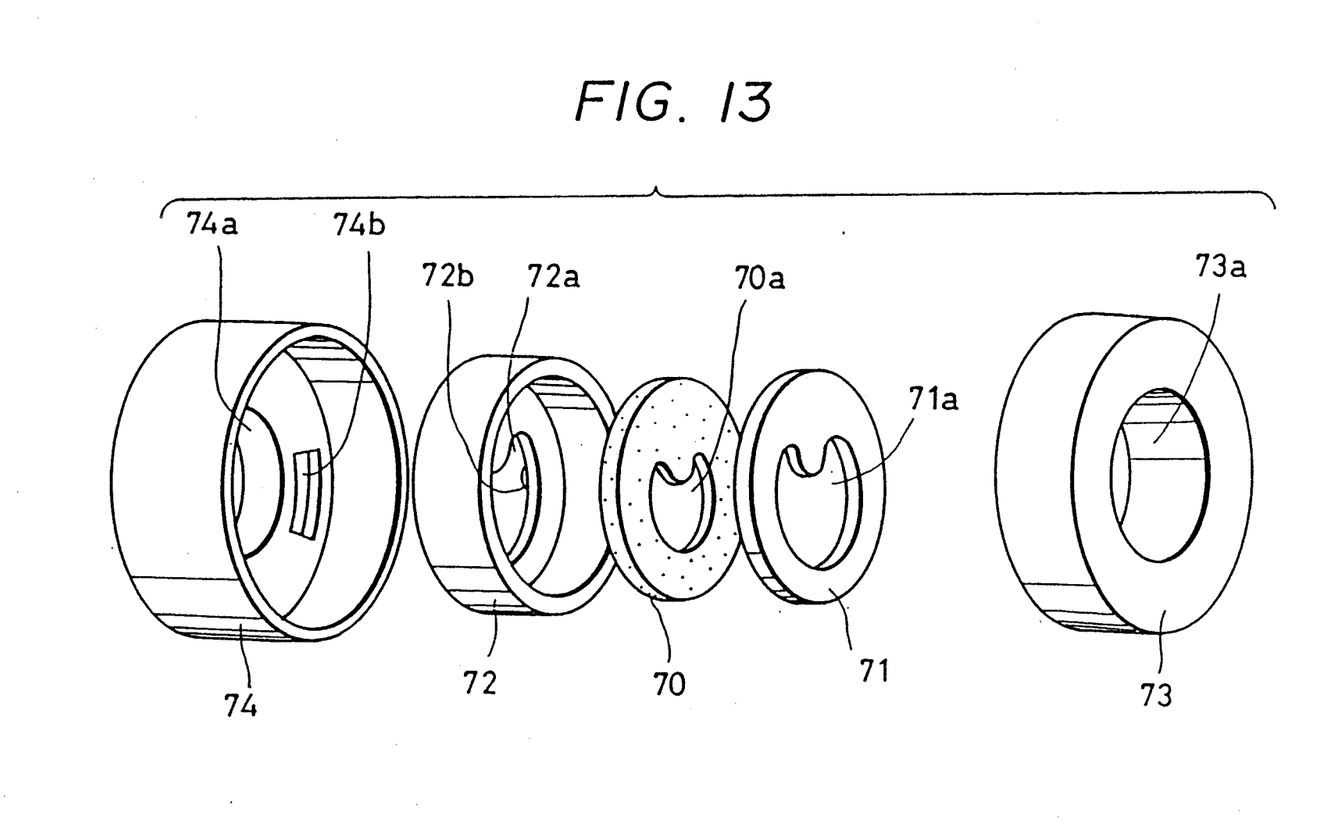
FIG. 13 is an enlarged exploded perspective view of the packing unit.

FIG. 11 is an enlarged sectional view of the packing unit 33, and FIG. 13 is an exploded perspective view of the packing unit 33.

In the figures, reference numeral 70 denotes a packing which is formed from an airproof, flexible and elastic material, for example, expanded sponge that has a large number of minute closed cells, or silicon rubber. The packing 70 has a bore 70a which has the same cross-sectional configuration as that of the insert tube 1 and a slightly smaller size than the cross-sectional size of the insert tube 1. Thus, the packing 70 can hermetically seal the outer periphery of the insert tube 1, without any gap, and the insert tube 1 can be smoothly inserted into and removed from the packing 70 without being caught therein.

A packing gland 71 and a packing retainer 72, which are formed from a rigid material, have bores 71a and 72a, which have a slightly larger size than the cross-sectional size of the insert tube 1. The packing gland 71 is formed in the shape of a lid, while the packing retainer 72 has a tubular outer wall portion. The packing 70 is clamped between the packing gland 71 and the inner side of the bottom of the packing retainer 72. A small projection 72b is provided on the outer side of the bottom of the packing retainer 72.

A cap ring 73 and a holder 74 have circular bores 73a and 74a, which have a diameter that is substantially equal to those of the bores 71a and 72a. A projection 74c (FIG. 11), which is provided on the holder 74, fits into a bore 37 that is formed in the mouth portion 23 to serve for positioning and prevention of rotation of the packing unit 33.

The holder 74, which is formed in a tubular shape, accommodates the packing 70, the packing gland 71 and the packing retainer 72 as one unit and is lidded with the cap ring 73. The cap ring 73 is bonded to the wall of the control part inserting bore 32.

The holder 74 is formed with a guide groove 74b. The projection 72b of the packing retainer 72 is movable within the guide groove 74b. Accordingly, within this movable range the packing 70 is movable in the radial direction of the insert tube 1 and rotatable about the axis of the insert tube 1, that is, about the center of the bore 70a, together with the packing gland 71 and the packing retainer 72.

Figure 12A:
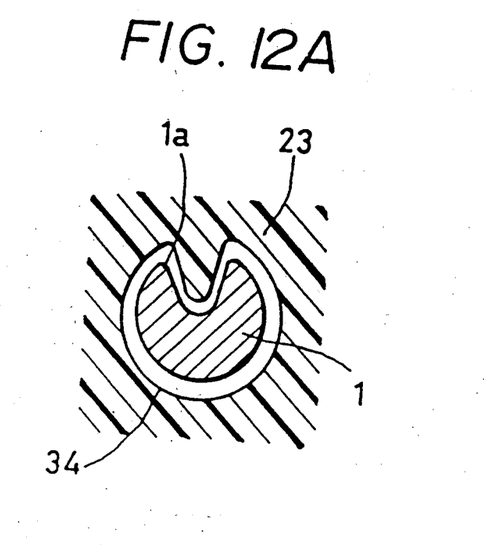
FIGS. 12A and 12B are sectional views taken along the line XII—XII in FIG. 11.
Figure 12B:
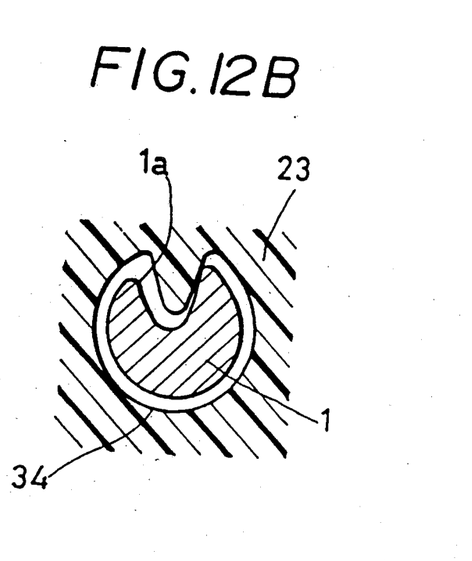

FIG. 12A is a sectional view taken along the line XII—XII of FIG. 11, showing a state where the insert tube 1 of the endoscope is inserted straight in the mouth portion 23. If, in this state, the insert tube 1 is turned about its axis, it can be rotated until the groove 1a in the insert tube 1 comes into contact with the U-shaped wall portion of the insert tube inserting bore 34, as shown in FIG. 12B.

Use of the sheath device according to the above-described embodiment will next be explained.

When the insert tube 1 of the endoscope is inserted a little into the insert tube inserting bore 34 through the packing unit 33 in the sheath 20, the outer periphery of the insert tube 1 is hermetically sealed by the packing 70, without any gap. In this state, air is supplied into the sheath 20 from the air supply opening 35 to inflate the tubular portion 21. After the tubular portion 21 has inflated, the insert tube 1 is further inserted into the sheath 20.

Figure 14:
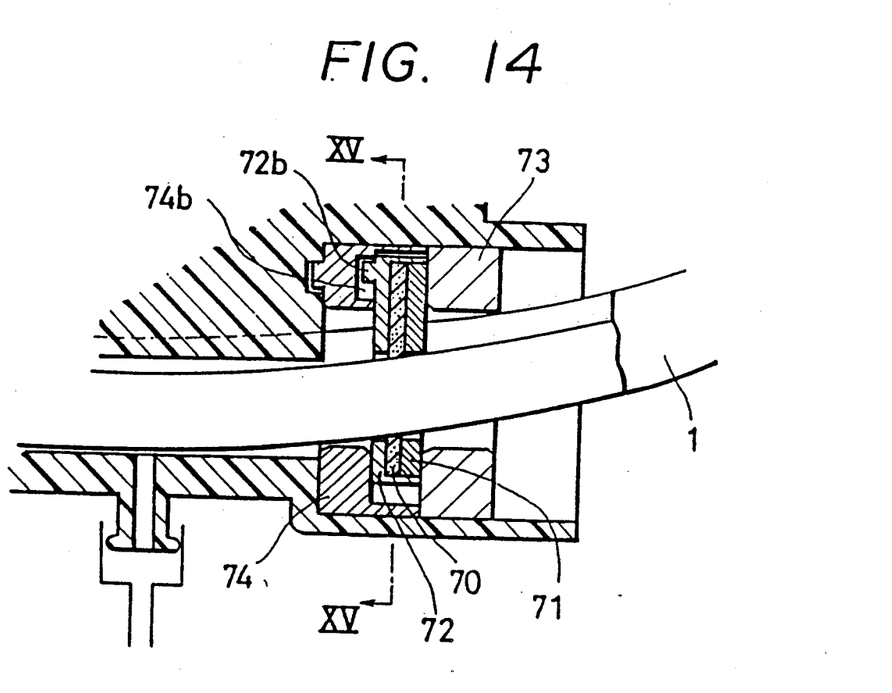
FIG. 14 is an enlarged sectional side view of the packing unit in the sheath device, which is in use.
Figure 15A:
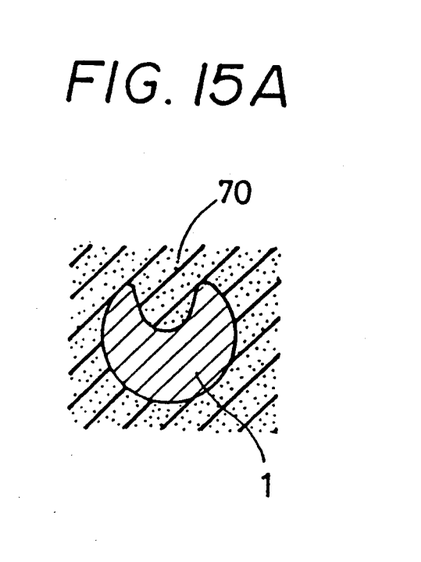
FIGS. 15A and 15B are sectional views taken along the line XV—XV in FIG. 14.
Figure 15B:
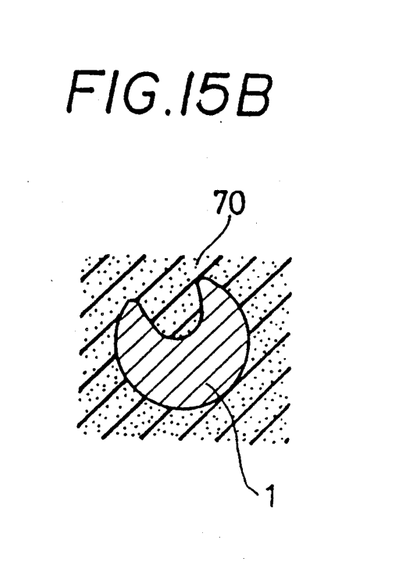

At this time, even if the insert tube 1 is bent, as shown in FIG. 14, the packing 70 moves radially along with the insert tube 1. Accordingly, no gap is produced between the packing 70 and the insert tube 1 and there is therefore no possibility that air will leak out from the sheath 20. Even if the insert tube 1, which is inserted straight through the packing 70, as shown in FIG. 15A, is twisted, the packing 70 rotates in response to the twisting, as shown in FIG. 15B. Accordingly, no gap is produced between the packing 70 and the insert tube 1 and no air leaks out.

After the insert tube 1 has been completely inserted into the sheath 20, the channel connector 26 is connected to the connector socket 13. In consequence, the air sending channel 24a is connected to the air supply channel 10, and the water sending channel 24w is connected to the water supply channel 9.

In addition, the suction channel tube 30, which extends rearwardly of the channel connector 26, is fitted into the suction channel guide groove 15. Thus, the end face of the distal end portion 22 can be sprayed with air and water by operating the air and water control valve 7, and suction can be performed from the distal end of the sheath 20 by operating the suction control valve 8. If a tool for an endoscopic procedure, for example, a biopsy forceps, is inserted from the forceps inserting bore 28, a bioptic procedure can be conducted through the suction channel 24s.

After the use of the endoscope, the suction channel tube 30 is removed from the suction channel guide groove 15, and the channel connector 26 is removed from the connector socket 13. Thereafter, air is supplied from the air supply opening 35 to inflate the tubular portion 21, and the insert tube 1 of the endoscope is then removed from the sheath 20.

It should be noted that the configuration of the bore 70a in the packing 70 is not necessarily limited to in the above-described embodiment and that any configuration which corresponds to the cross-sectional configuration of the insert part of the endoscope may be employed.

According to the present invention, since the channels in the sheath device for the endoscope can be simultaneously connected to the corresponding conduits in the endoscope, the connection of the channels is facilitated. As a result, it is possible to eliminate any danger that the endoscope may be contaminated when the sheath device is removed therefrom.

Since the channels can be simultaneously connected and disconnected, it is possible to employ a conventional valve mechanism for endoscopes.

Since the channels which are provided in the endoscope and those which are provided in the sheath device are disposed substantially parallel to each other and connected to each other in a direction which is perpendicular to the axes of these channels, there is no need to ensure a long space for the connection of these channels. Consequently, it is possible to make the connecting device compact, reduce the overall size of the control part of the endoscope and obtain superior operability.

In the sheath device of the present invention, even if the insert tube of the endoscope is bent or rotated about its axis, the packing moves, following the movement of the insert tube, so that no gap is produced between the packing and the insert tube. Accordingly, no air leaks out from the sheath, and the insert tube can be smoothly inserted into and removed from the sheath.

While the invention has been described by reference to specific embodiments chosen for purposes of illustration, it should be apparent that numerous modifications could be made thereto by those skilled in the art without departing from the basic concept and scope of the invention.

We claim:

1. A sheath device for an endoscope, which is removably fitted over an insert tube of said endoscope to isolate said insert tube from the external environment, comprising:
   a sheath which removably covers said insert tube to isolate it from the external environment;
   a plurality of channels for passing fluids, each channel having an opening at one end near the distal end portion of said sheath; and
   a channel connecting means provided at proximal end portions of said channels near the proximal end portion of said sheath, and capable of simultaneously connecting at least two of said channels to respective conduits in said endoscope.

2. A sheath device for an endoscope according to claim 1, wherein said channels include a channel for passing air and a channel for passing water, which are connected to respective conduits in said endoscope through said channel connecting means.

3. A sheath device for an endoscope according to claim 2, wherein said channel connecting means has a double-conduit structure which comprises a pair of inner and outer conduits, through which said channel for passing air and said channel for passing water are connected to the respective conduits in said endoscope.

4. A sheath device for an endoscope according to claim 1, wherein said channels include a suction channel for effecting suction through an opening that is provided in the distal end portion of said sheath, said suction channel not being connected to any of the conduits in said endoscope within said channel connecting means but extending along a path independent of the connection between said channels and said conduits.

5. A sheath device for an endoscope according to claim 1, wherein said sheath has a forceps inserting bore for passing a tool for an endoscopic procedure through the insert tube, said forceps inserting bore being provided in the vicinity of the proximal end portion of said sheath.

6. A sheath device for an endoscope according to claim 5, wherein said forceps inserting bore is provided at its mouth with an automatic forceps stopper which is normally closed but forced open in response to the insertion of said tool for an endoscope procedure.

7. A channel tube for an endoscope, which is removably fitted in an insert tube of said endoscope, comprising:
   a plurality of channels for passing fluids, each channel opening at one end thereof to the outside at the distal end portion of said channel tube; and
   a channel connecting means which is provided at the proximal end portions of said channels and which is capable of simultaneously connecting at least two of said channels to respective conduits in said endoscope.

8. A structure for connecting fluid conduits in a sheath device to fluid conduits in an endoscope, said sheath device removably covering an insert tube of said endoscope to isolate said insert tube from the external environment, comprising:
   a plurality of channels for passing fluids, each channel opening at one end thereof to the outside at the distal end portion of said sheath device; and
   a channel connecting means which is capable of simultaneously connecting at least two of said channels to respective conduits in said endoscope.

9. A fluid conduit connecting structure according to claim 8, wherein said channels include a channel for passing air and a channel for passing water, which are connected to respective conduits in said endoscope through said channel connecting means.

10. A structure for connecting fluid conduits in a channel tube to fluid conduits in an endoscope, which is removably fitted in an insert part of said endoscope, comprising:
    a plurality of channels for passing fluids, each channel opening at one end thereof to the outside at the distal end portion of said channel tube; and
    a channel connecting means which is capable of simultaneously connecting at least two of said channels to respective conduits in said endoscope.

11. A structure for connecting fluid conduits in an endoscope, comprising:
    a fluid supply channel which is disposed inside a control part of said endoscope;
    a fluid sending channel which is provided in a sheath device that removably covers an insert tube of said endoscope, to send out a fluid that is supplied from said fluid supply channel; and
    a channel connecting means for connecting together said fluid supply channel and said fluid sending channel through a connecting conduit in said control part of said endoscope, with the respective end portions of said channels being disposed substantially parallel to each other, and said connecting conduit being disposed in a direction which is perpendicular to the axes of said end portions of said channels.

12. A fluid conduit connecting structure according to claim 11, wherein said fluid supply channel and said fluid sending channel are detachable in said channel connecting means.

13. A fluid conduit connecting structure according to claim 11, wherein said fluid supply and sending channels include, respectively, channels for passing air and channels for passing water, said channel connecting means having a double-conduit structure which comprises a pair of inner and outer conduits, through which said channels for passing air and said channels for passing water are simultaneously connected to each other.

14. A structure for connecting fluid conduits in an endoscope, comprising:
    a fluid supply channel which is disposed inside a control part of said endoscope;
    a fluid sending channel which is provided in a channel tube that is removably fitted over an insert tube of said endoscope, to send out a fluid that is supplied from said fluid supply channel; and
    a channel connecting means for connecting together said fluid supply channel and said fluid sending channel through a connecting conduit in said control part of said endoscope, with the respective end portions of said channels being disposed substantially parallel relation to each other, and said connecting conduit being disposed in a direction which is perpendicular to the axes of said end portions of said channels.

15. A sheath device for an endoscope, which removably covers an insert tube of said endoscope to isolate said insert tube from the external environment, comprising:
  an airproof sheath which removably covers said insert tube; and
  a packing which is provided in an opening at the proximal end of said sheath in such a manner as to be movable in the radial direction of said sheath to enable said insert tube to be inserted into and removed from said sheath with the outer peripheral surface of said insert tube being hermetically sealed, without any gap between said packing and said outer peripheral surface.

16. A sheath device for an endoscope, which removably covers an insert tube of said endoscope to isolate said insert tube from the external environment, comprising:
  an airproof sheath which removably covers said insert tube;
  an air supply opening for supplying air into said sheath to inflate it; and
  a packing which is provided in an opening at the proximal end of said sheath in such a manner as to be movable in the radial direction of said sheath to enable said insert tube to be inserted into and removed from said sheath with the outer peripheral surface of said insert tube being hermetically sealed, without any gap between said packing and said outer peripheral surface.

17. A sheath device for an endoscope according to claim 16, wherein said packing is formed from a flexible and elastic material and has a bore with a slightly smaller size than the cross-sectional size of said insert tube.

18. A sheath device for an endoscope according to claim 16, wherein said packing has a bore and is rotatable about the center of said bore.

19. A sheath device for an endoscope according to claim 17, wherein said packing is clamped between a pair of rigid members which are each provided with a bore with a slightly larger size than the cross-sectional size of said insert tube.

20. A sheath device for an endoscope according to claim 19, wherein said packing is rigidly secured to said pair of rigid members and movable together with them as one unit.

21. A sheath device for an endoscope according to claim 20, wherein said packing and said pair of rigid members are rotatable together as one unit about the center of said bore that is formed in said packing.

22. A sheath device which removably covers an object which is inserted therein to isolate said object from the external environment, comprising:
  an airproof sheath which removably covers said object; and
  a packing which is provided in an opening at the proximal end of said sheath in such a manner as to be movable in the radial direction of said sheath to enable said object to be inserted into and removed from said sheath with the outer peripheral surface of said object being hermetically sealed, without any gap between said packing and said outer peripheral surface.

23. A sheath device which removably covers an object which is inserted therein to isolate said object from the external environment, comprising:
  an airproof sheath which removably covers said object;
  an air supply opening for supplying air into said sheath to inflate it; and
  a packing which is provided in an opening at the proximal end of said sheath in such a manner as to be movable in the radial direction of said sheath to enable said object to be inserted into and removed from said sheath with the outer peripheral surface of said object being hermetically sealed, without any gap between said packing and said outer peripheral surface.

24. A sheath device according to claim 23, wherein said packing is formed from a flexible and elastic material and has a bore with a slightly smaller size than the cross-sectional size of said object.

25. A bag device which removably covers an object which is inserted therein to isolate said object from the external environment, comprising:
  an airproof bag which removably covers said object; and
  a packing which is provided in an opening at the proximal end of said bag in such a manner as to be movable in the radial direction of said bag to enable said object to be inserted into and removed from said bag with the outer peripheral surface of said object being hermetically sealed, without any gap between said packing and said outer peripheral surface.

* * * * *

UNITED STATES PATENT AND TRADEMARK OFFICE
CERTIFICATE OF CORRECTION

PATENT NO. : 4,991,565
DATED : February 12, 1991
INVENTOR(S) : Nagashige TAKAHASHI et al.

It is certified that error appears in the above-indentified patent and that said Letters Patent is hereby corrected as shown below:

At column 9, line 57 (claim 6, line 5), change "endoscope" to --- endoscopic---.

Signed and Sealed this

Sixteenth Day of January, 1996

Attest:

BRUCE LEHMAN

Attesting Officer

Commissioner of Patents and Trademarks